United States Patent

Pitet et al.

Patent Number: 5,198,441
Date of Patent: Mar. 30, 1993

[54] DERIVATIVES OF 1,2-DIHYDRO 2-OXO QUINOXALINES, THEIR PREPARATION AND THEIR USE IN THERAPY

[75] Inventors: Guy Pitet; Christian Faure, both of Toulouse; Francoise Couret, Corransac; Dennis Bigg; Jean-Pierre Tarayre, both of Castres, all of France

[73] Assignee: Pierre Fabre Medicament, Boulogne, France

[21] Appl. No.: 688,536

[22] PCT Filed: Oct. 17, 1990

[86] PCT No.: PCT/FR90/00752

§ 371 Date: Jun. 17, 1991

§ 102(e) Date: Jun. 17, 1991

[87] PCT Pub. No.: WO91/05772

PCT Pub. Date: May 2, 1991

[30] Foreign Application Priority Data

Oct. 23, 1989 [FR] France .................. 89 13961

[51] Int. Cl.[5] .................. C07D 241/44; A61K 31/495
[52] U.S. Cl. ........................ 514/249; 544/354
[58] Field of Search .................. 544/354; 514/249

[56] References Cited

U.S. PATENT DOCUMENTS

| | | | |
|---|---|---|---|
| 4,140,789 | 2/1979 | Jaeggi et al. ............... | 544/354 |
| 4,181,724 | 1/1980 | Hall et al. ................. | 424/250 |
| 5,034,537 | 7/1991 | Frazee ..................... | 548/252 |

FOREIGN PATENT DOCUMENTS

| | | | |
|---|---|---|---|
| 728649 | 2/1966 | Canada ..................... | 544/354 |
| 32564 | 7/1981 | European Pat. Off. . | |
| 242957 | 10/1987 | European Pat. Off. . | |
| 2277 | 1/1982 | Japan ...................... | 544/354 |

OTHER PUBLICATIONS

"Advanced Organic Chemistry" (2nd ed.) by Jerry March, pp. 361-362 (1977).

Primary Examiner—Nicholas S. Rizzo
Assistant Examiner—E. Bernhardt
Attorney, Agent, or Firm—Gordon W. Hueschen

[57] ABSTRACT

New derivatives of 1,2-dihydro 2-oxo quinoxalines corresponding to the general formula I:

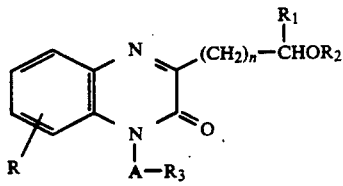

in which:
R is a hydrogen or halogen atom
$R_1$ is a hydrogen atom or a straight or branched $C_1$-$C_4$ alkyl radical
$R_2$ is:
  a hydrogen atom
  a $C(O)R_4$ radical in which $R_4$ is a straight or branched $C_1$-$C_4$ alkyl group
  a $C(O)NHR_5$ radical in which $R_5$ is a straight or branched $C_1$-$C_4$ alkyl radical or a phenyl group
A is a $C_1$-$C_4$ alkaline chain
$R_3$ represents:
  a hydrogen atom, a $C_1$-$C_4$ alkyl radical, a $C_3$-$C_6$ cycloalkyl radical, an alcynyl, nitrile, hydroxyl, carboxamido, pyridyl, phenyl group, or a phenyl group substituted by a halogen atom, a $C_1$-$C_4$ alkyl group, a $C_1$-$C_4$ alkoxy group or a nitro group
  an alkenyl radical of the formula:

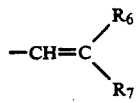

in which $R_6$, $R_7$ may, independently of each other, be a hydrogen atom, a $C_1$-$C_4$ alkyl group, a phenyl group or an alkoxycarbonyl group
a radical of the formula:

—OC(O)$R_8$ in which $R_8$ represents a $C_1$-$C_4$ alkyl radical
a radical of the formula:

—OC(O)NHR$_9$ in which $R_9$ represents a straight or branched $C_1$-$C_4$ alkyl group, or a phenyl group
may assume values from 2 to 4.

as well as the therapeutically acceptable organic or inorganic salts of these molecules. The compounds are useful in the treatment of respiratory disorders.

5 Claims, No Drawings

DERIVATIVES OF 1,2-DIHYDRO 2-OXO QUINOXALINES, THEIR PREPARATION AND THEIR USE IN THERAPY

The object of the present invention is new derivatives of 1,2-dihydro 2-oxo quinoxalines, their preparation and their use in therapy.

The compounds of the invention have general formula I:

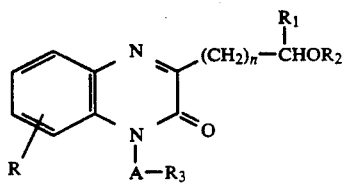

in which
R is a hydrogen or halogen atom
$R_1$ is a hydrogen atom or a straight or branched $C_1$-$C_4$ alkyl radical,
$R_2$ is:
  a hydrogen atom
  a C(O)$R_4$ radical in which $R_4$ is a straight or branched $C_1$-$C_4$ alkyl group
  a C(O)NH$R_5$ radical in which $R_5$ is a straight or branched $C_1$-$C_4$ alkyl group or a phenyl group
A is a $C_1$-$C_4$ alkylene chain
$R_3$ is:
  a hydrogen atom, a $C_1$-$C_4$ alkyl radical, a $C_3$-$C_6$ cycloalkyl radical, an alkylnyl, nitrile, hydroxyl, carboxamido, pyridyl, phenyl group, or phenyl group substituted by a halogen atom, a $C_1$-$C_4$ alkyl group, a $C_1$-$C_4$ alkoxy group or a nitro group
  an alkenyl radical of the formula:

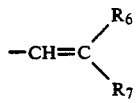

in which $R_6$, $R_7$ may, independently of each other, be a hydrogen atom, a $C_1$-$C_4$ alkyl group, a phenyl group or an alkoxycarbonyl group
a radical of the formula:

—OC(O)$R_8$ in which $R_8$ represents a $C_1$-$C_4$ alkyl radical
a radical of the formula:

—OC(O)NH$R_9$ in which $R_9$ represents a straight or branched $C_1$-$C_4$ alkyl group or a phenyl group
n may assume values from 2 to 4.

Furthermore, the invention covers the salts of compounds of general formula I with pharmaceutically acceptable acids in the case of compounds having sufficient basicity.

The compounds of general formula I ($R_2$=H) of the invention can be prepared in accordance with the following reaction mechanism:

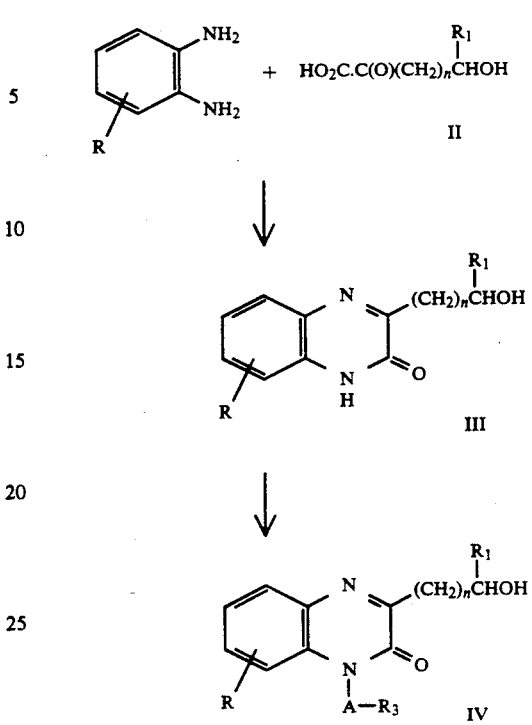

The initial keto acids of formula II can be obtained by known methods, for instance the method described by Korte et al., Chem. Ber. 92, 877–83 (1959).

The reaction of the keto acid of formula II with an orthophenylene diamine is preferably carried out in an alcoholic solvent such as ethanol, or an acid solvent such as acetic acid. The reaction can be carried out at room temperature or at a temperature ranging up to the boiling point of the solvent.

The 1,2-dihydro 2-oxo quinoxalines of general formula III thus obtained are then treated by a reagent $R_3$-A-X and which $R_3$ in A are defined as above and X represents a nucleofuge atom such as iodine, chlorine, bromine or a mesylate or tosylate group, in the presence of a base such as sodium hydroxide. The reaction is carried out within an aprotic solvent such as DMF.

The quinoxalines of formula IV which are thus obtained correspond to the compounds of formula I in which $R_2$ represents a hydrogen atom.

In order to prepare a compound of formula I in which $R_2$ represents a group of the formula —C(O)$R_4$ ($R_4$ being defined as above), the compound of formula IV is reacted with an excess of anhydride of formula ($R_4$CO)$_2$O, preferably in the hot. A compound of formula I can also be prepared in which $R_2$ represents a group of the formula —C(O)$R_4$ by reacting a compound of general formula III with an excess of anhydride of formula ($R_4$CO)$_2$O and then alkylating this product by a reagent of the formula $R_3$-A-X in a manner similar to that described above.

In order to prepare a compound of formula I in which $R_2$ represents a group of formula —C(O)NH$R_5$ ($R_5$ being defined as above), a compound of formula IV is reacted with an isocyanate of formula $R_5$NCO in an aprotic solvent such as toluene at a temperature ranging up to the boiling point of the solvent, or else a compound of formula IV is reacted with phosgene in an aprotic solvent, for instance toluene, and then with an amine of formula $R_5NH_2$.

In order to prepare a compound of formula I in which $R_3$ represents a radical $-OC(O)R_8$ ($R_8$ being defined as above), a compound of formula I in which $R_3$ represents a hydroxyl group can be reacted with an excess of anhydride of formula $(R_8CO)_2O$, preferably in the hot.

In order to prepare a compound of formula I in which $R_3$ represents a radical $-OC(O)NHR_9$ ($R_9$ being defined as above), a compound of formula I in which $R_3$ represents a hydroxyl group can be reacted with an isocyanate of formula $R_9NCO$ in an aprotic solvent such as toluene or xylene at the reflux temperature of the solvent.

The following examples illustrate the invention without, however, limiting its scope.

The analyses and the RMN and IR spectra confirm the structure of the compounds obtained in accordance with the invention.

EXAMPLE 1

1-prenyl 3-(3-hydroxy propyl) 1,2-dihydro 2-oxo quinoxaline [I; $R=R_1=R_2=H$, $n=2$, $A=CH_2$, $R_3=CH=C(CH_3)_2$]: compound 1.

1.1 3-(3-hydroxy propyl) 1,2-dihydro 2-oxo quinoxaline

To a solution of 43 g of 5-hydroxy 2-oxo pentanoic acid in 430 ml of ethanol there are added 35 g of orthophenylene diamine. The mixture is agitated overnight at room temperature and then evaporated to dryness in a vacuum. The brown residue obtained is dissolved in 400 ml of 2N caustic soda. After filtration through a bed of celite, the filtrate is acidified by 80 ml of concentrated hydrochloric acid; the light brown solid is filtered and then recrystallized from 500 ml of ethanol. After being placed overnight in a refrigerator, filtered and then dried under vacuum at 70° C., 36.15 g of beige-colored crystals of 3-(3-hydroxy propyl) 1,2-dihydro 2-oxo quinoxaline are isolated.

M.P. 200° C. (Kofler)
Yield: 55%
IR (C=O): 1650 cm$^{-1}$ 1.2 1-prenyl 3-(3-hydroxy propyl) 1,2-dihydro 2-oxo quinoxaline: compound 1.

To a suspension of 9.68 g of 60% sodium hydride in 50 ml of anhydrous DMF, there is slowly added a solution of 44.9 g of 3-(3-hydroxy propyl) 1,2-dihydro 2-oxo quinoxaline (obtained in accordance with 1.1) in 450 ml of DMF. The solution is agitated until completion of the liberation of hydrogen, whereupon 36 g of prenyl bromide are added. The resultant solution is agitated overnight at room temperature and then evaporated to dryness under reduced pressure. The brown residue is treated with 150 ml of water and 400 ml of methylene chloride. After evaporation under vacuum, a beige solid is obtained which is recrystallized from 200 ml of toluene. In this way there are isolated 33.8 g of compound 1 in the form of pale yellow crystals.

M.P. 97° C. (Kofler)
Yield: 56%
IR (C=O): 1655 cm$^{-1}$

EXAMPLE 2

1-allyl 3-(3-acetoxy butyl) 1,2-dihydro 2-oxo quinoxaline [I; $R=H$, $R_1=CH_3$, $R_2=C(O)CH_3$, $n=2$, $A=CH_2$, $R_3=-CH=CH_2$]: compound 2.

2.1 3-(3-acetoxy butyl) 1,2-dihydro 2-oxo quinoxaline

In a 100 ml round-bottomed flask provided with magnetic agitation and a reflux condenser on top of which there is a $CaCl_2$ trap, there is placed 1 g of 3-(3-hydroxy butyl) 1,2-dihydro 2-oxo quinoxaline, obtained by a method similar to that described in Example 1. 10 ml of acetic anhydride are added and heating is effected under reflux for two hours. It is allowed to cool and then, after addition of 10 ml of water, heated at 60° C. for 30 minutes. The solid obtained after evaporation of the solvent is recrystallized from ethanol, giving 0.8 g of the acetylated derivative.

M.P. 138° C. (Kofler)
IR (C=O): 1655 cm$^{-1}$, 1680 cm$^{-1}$ 2.2 1-allyl 3-(3-acetoxy butyl) 1,2-dihydro 2-oxo quinoxaline: compound 2.

0.75 g of 50% sodium hydroxide is added to a solution of 3.9 g of 3-(3-acetoxy butyl) 1,2-dihydro 2-oxo quinoxaline (obtained in accordance with 2.1) in 100 ml of DMF. After agitation for two hours, 3 ml of allyl bromide are added and agitation is continued for 16 hours. The reaction mixture is concentrated under vacuum and diluted with water before extraction with the methylene chloride. The brown oil obtained after drying and evaporation of the methylene chloride is purified by chromatography over silica gel (elution: isopropyl ether and then ethyl ether) to give 3 g of compound 2 in the form of an oil.

Yield: 66.7%
IR: 1660 cm$^{-1}$ (2-oxo); 1735 cm$^{-1}$ (OC(O)CH$_3$)

EXAMPLE 3

1-propyl 3-(3-methylcarbamoyloxy propyl) 1,2-dihydro 2-oxo quinoxaline [I; $R=R_1=H$, $R_2=C(O)NHCH_3$, $n=2$, $A=CH_2$, $R_3=CH_2CH_3$]: compound 3.

Method A 16.2 g of 1-propyl 3-(3-hydroxy propyl) 1,2-dihydro 2-oxo quinoxaline obtained in a manner similar to that described in the case of compound 1 are added to 80 ml of a 20% solution of phosgene in toluene. Agitation is effected for one hour at room temperature, whereupon evaporation to dryness is effected under vacuum and 25 ml are added of a 33% solution of methylamine in ethanol and 100 ml of anhydrous benzene. The reaction mixture is agitated overnight at room temperature and evaporated to dryness, and the residue taken up with 100 ml of water and 200 ml of methylene chloride.

After decantation, the organic phase is dried over sodium sulfate, filtered, and evaporated to dryness and the solid obtained is recrystallized from 100 ml of isopropanol. 9.86 g of compound 3 are obtained in the form of white crystals.

M.P. 115° C. (Kofler)
Yield: 49.5%
IR: 1650 cm$^{-1}$ (2-oxo); 1695 cm$^{-1}$ (carbamate)

Method B

In a 250 ml round-bottom flask provided with a magnetic agitator, a reflux condenser and a $CaCl_2$ trap there are placed 5.7 g of 1-propyl 3-(3-hydroxy propyl) 1,2-dihydro 2-oxo quinoxaline dissolved in 60 ml of anhydrous toluene. 1.58 g (1.64 ml) of methyl isocyanate is added and heating is effected overnight under reflux. Evaporation is effected to dryness under vacuum, and the solid obtained is crystallized from ethanol. 3 g of compound 3 are obtained in the form of white crystals.

M.P. 115° C. (Kofler)
Yield: 43%
IR: 1650 cm$^{-1}$ (2-oxo); 1695 cm$^{-1}$ (carbamate)

EXAMPLE 4

1-(2-methylcarbamoyloxy ethyl) 3-(3-hydroxy butyl) 1,2-dihydro 2-oxo quinoxaline [I; R=H, R$_1$=CH$_3$, R$_2$=H, n=2, A=CH$_2$CH$_2$, R$_3$=—OC(O)NHCH$_3$]: compound 4.

Into a 250 ml round-bottom flask provided with a magnetic agitator, a reflux condenser and a CaCl$_2$ trap, there is introduced a solution of 5.09 g of 1-(2-hydroxy ethyl) 3-(3-hydroxy butyl) 1,2-dihydro 2-oxo quinoxaline in 50 ml of anhydrous xylene. 1.35 g (1.4 ml) of methyl isocyanate is added and heating is effected under reflux for 3 hours. The solvent is evaporated and the residue obtained is chromatographed over silica gel (eluant CH$_2$Cl$_2$/MeOH=95:5). The fraction corresponding to an Rf of 0.42 (silica CHCl$_3$/MeOH=95:5) is isolated and then crystallized in 30 ml of toluene to give 1.54 g of compound 4 in the form of pale yellow crystals.

M.P. 136° C. (Kofler)
Yield: 25%
IR: 1645 cm$^{-1}$ (2-oxo); 1700 cm$^{-1}$ (carbamate)

The following table summarizes the main products synthesized, which illustrate the invention without however limiting its scope.

various products in accordance with the following protocol.

A piece of the trachea of a male tri-color guinea pig of an average weight of 400 g is cut in a spiral and mounted (about 2.5 cm) in an isolated organ cell maintained thermostatically at 37° C. and filled with oxygenated tyrode. The isometric contractions caused by the different mediators are recorded by means of a Gould Statham UC2 detector (Gould Inc. Oxnard, Calif., USA) or UF1 Palmer Bioscience detector connected to a potentiometric recorder (Linseiss, Selb, Federal Republic of Germany). At the start of the experiment, the piece of trachea was placed under a tension of 1 g and set aside for one hour.

The following mediator concentrations are used (concentrations generally causing maximum contraction): histamine dihydrochloride, 10 μg/ml; acetylcholine chloride, 1 μg/ml; potassium salt of leucotrine D$_4$, 0.05 μg/ml; potassium chloride, 1850 μg/ml. The concentrations of agents used produce contractions which become maximum within 5 to 15 minutes, depending on the mediators, and then remain at that level. One concentration of the product studied is administered for each contraction, and the product is left in contact with the trachea for 5 minutes. The inhibition, if any, obtained at the end of this time is measured (percentage variation in the amplitude of the contraction). The trachea is then washed for 15 seconds and set aside for about 10 minutes (time necessary to return to the base tone) before causing a new contraction.

TABLE 1

| Compound No. | R | R$_1$ | R$_2$ | R$_3$ | n | A | MP (°C.) |
|---|---|---|---|---|---|---|---|
| 1 | H | H | H | —CH=C(CH$_3$)$_2$ | 2 | CH$_2$ | 97 |
| 2 | H | CH$_3$ | —C(O)CH$_3$ | —CH=CH$_2$ | 2 | CH$_2$ | |
| 3 | H | H | —C(O)NHCH$_3$ | —CH$_2$CH$_3$ | 2 | CH$_2$ | 115 |
| 4 | H | CH$_3$ | H | —OC(O)NHCH$_3$ | 2 | CH$_2$CH$_2$ | 136 |
| 5 | Cl-7 | H | H | —CH=CH$_2$ | 2 | CH$_2$ | 111 |
| 6 | Cl-6 + Cl-7 | H | H | —C≡CH | 2 | CH$_2$ | 126 |
| 7 | H | H | H | —CH=CH$_2$ | 3 | CH$_2$ | 62 |
| 8 | H | H | H | —CH=CH$_2$ | 2 | CH$_2$ | 94 |
| 9 | H | CH$_3$ | H | —CH=CH$_2$ | 2 | CH$_2$ | 80 |
| 10 | Cl-6 + Cl-7 | H | H | —CH=CH.CO$_2$CH$_3$ | 2 | CH$_2$ | 143 |
| 11 | H | H | H | —CH$_3$ | 2 | CH$_2$CH$_2$ | 69 |
| 12 | H | H | H | —CH=CH.CH$_3$ | 2 | CH$_2$ | 68 |
| 13 | H | H | H | —C≡CH | 2 | CH$_2$ | 125 |
| 14 | H | H | H | —CH=CH.Ph | 2 | CH$_2$ | 111 |
| 15 | H | H | H | cyclopropyl | 2 | CH$_2$ | 95 |
| 16 | H | H | H | —CN | 2 | CH$_2$ | 144 |
| 17 | H | H | H | phenyl | 2 | CH$_2$ | 105 |
| 18 | H | H | H | —CONH$_2$ | 2 | CH$_2$ | 223 |
| 19 | H | CH$_3$ | H | —CH=CH.CH$_3$ | 2 | CH$_2$ | 76 |
| 20 | H | CH$_3$ | H | —CH=C(CH$_3$)$_2$ | 2 | CH$_2$ | 85 |
| 21 | H | CH$_3$ | H | cyclopropyl | 2 | CH$_2$ | 76 |
| 22 | H | H | H | (NO$_2$)-4 phenyl | 2 | CH$_2$ | 176 |
| 23 | H | CH$_3$ | H | CH$_3$ | 2 | CH$_2$CH$_2$ | Oil |
| 24 | H | CH$_3$ | H | (CH$_3$O)-4 phenyl | 2 | CH$_2$ | 134 |
| 25 | H | CH$_3$ | H | H | 2 | CH$_2$ | 95 |
| 26 | H | CH$_3$ | H | CH$_3$ | 2 | CH$_2$CH$_2$CH$_2$ | Oil |
| 27 | H | CH$_3$ | H | pyridyl-2 | 2 | CH$_2$ | 180 (.HCl) |
| 28 | H | CH$_3$ | H | CH$_3$ | 2 | (CH$_2$)$_4$ | Oil |
| 29 | H | CH$_3$ | H | CH$_2$CH$_3$ | 2 | (CH$_2$)$_4$— | Oil |
| 30 | H | CH$_3$ | H | pyridyl-3 | 2 | CH$_2$ | 135 (base) 203 (.HCl) |
| 31 | H | CH$_3$ | H | pyridyl-4 | 2 | CH$_2$ | 170 (base) 190 (.HCl) |
| 32 | H | H | —C(O)NHCH$_3$ | —CH=CH.CH$_3$ | 2 | CH$_2$ | 98 |
| 33 | H | H | —C(O)NHPr$^i$ | CH$_3$ | 2 | CH$_2$CH$_2$ | 115 |
| 34 | H | H | —C(O)NHC$_6$H$_5$ | CH$_3$ | 2 | CH$_2$CH$_2$ | 117 |
| 35 | H | H | H | —OC(O)CH$_3$ | 2 | CH$_2$CH$_2$ | 82 |
| 36 | H | CH$_3$ | H | —OC(O)CH$_3$ | 2 | CH$_2$CH$_2$ | 69 |
| 37 | H | CH$_3$ | H | —OH | 2 | CH$_2$CH$_2$ | 131 |
| 38 | H | H | H | —OH | 2 | CH$_2$CH$_2$ | 123 |
| 39 | H | H | H | —CH=C(CH$_3$)$_2$ | 4 | CH$_2$ | 77 |

The compounds of the invention were subjected to pharmacological tests which have shown their interest as broncholytics. For this purpose, the compounds were studied for their effect against contractions caused by The water-insoluble products are diluted in 0.178% (v/v) (final concentration in the bath) of dimethyl sulfoxide (DMSO). This concentration of DMSO does not produce any effect with regard to the contractions of the various mediators studied.

The 50% inhibitory concentrations (IC 50) are calculated using an SAS program (Statistical Analysis System) based on Bliss and Cattel (Bliss C.I. and Cattel McK. Biological Assay Ann. Rev. Physiol. 5, 479, 1943).

The results obtained on some compounds of the invention are indicated by way of example in Tables 2 to 5.

TABLE 2

Antagonism of the effect of potassium chloride

| Compound No. | IC 50 (µg/ml) |
|---|---|
| 1 | 5.6 |
| 5 | 17 |
| 8 | 12.3 |
| 12 | 6.2 |
| theophylline | 21 |

TABLE 3

Antagonism of the effect of histamine

| Compound No. | IC 50 (µg/ml) |
|---|---|
| 1 | 0.9 |
| 3 | 3.3 |
| 11 | 3.45 |
| 12 | 0.54 |
| 17 | 0.43 |
| 19 | 1.13 |
| 20 | 1.55 |
| 24 | 1.3 |
| theophylline | 11.5 |

TABLE 4

Antagonism of the effect of acetylcholine

| Compound No. | IC 50 (µg/ml) |
|---|---|
| 1 | 25.5 |
| 3 | 7.1 |
| 12 | 15.5 |
| 19 | 16.5 |
| 20 | 9.7 |
| theophylline | 65 |

TABLE 5

Antagonism of the effect of leucotriene $D_4$

| Compound No. | % of inhibition at 10 µg/ml |
|---|---|
| 1 | −71 |
| 12 | −71 |
| 15 | −64 | theophylline IC 50 = 13.5 µg/ml

The compounds of the invention are broncholytics which can be used for the treatment of diseases such as chronic obstructive bronchopneumopathies, respiratory insufficiency, emphysema and cardiovascular pathologies relative to cardiac insufficiency.

The pharmaceutical compositions can be in suitable form for oral, rectal, parenteral or local administration, for instance in the form of capsules, tablets, granules, gels or liquid solutions, drinkable syrups or suspensions, aerosols or spray solutions, and contain suitable excipients. The dialy dose can range from 50 to 1000 mg.

We claim:

1. 1,2-dihydro 2-oxo quinoxalines selected from those of the formula I:

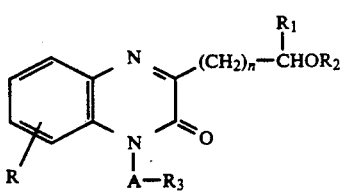

in which:
R represents a hydrogen or halogen atom
$R_1$ is a hydrogen atom or a straight or branched $C_1$-$C_4$ alkyl radical
$R_2$ is:
  a hydrogen atom
  a C(O)$R_4$ radical in which $R_4$ is a straight or branched $C_1$-$C_4$ alkyl group
  a C(O)NH$R_5$ radical in which $R_5$ is a straight or branched $C_1$-$C_4$ alkyl group or a phenyl group
A is a $C_1$-$C_4$ alkylene chain
$R_3$ is:
  a hydrogen atom, a $C_1$-$C_4$ alkyl radical, a $C_3$-$C_6$ cycloalkyl radical, an alkylnyl, nitrile, hydroxyl, carboxamido, pyridyl, phenyl group, or phenyl group substituted by a halogen atom, a $C_1$-$C_4$ alkyl group, a $C_1$-$C_4$ alkoxy group or a nitro group
  an alkenyl radical of the formula:

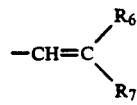

in which $R_6$, $R_7$ may, independently of each other, be a hydrogen atom, a $C_1$-$C_4$ alkyl group, a phenyl group or an alkoxycarbonyl group
  a radical of the formula:

in which $R_8$ represents a $C_1$-$C_4$ alkyl radical
  a radical of the formula:

in which $R_9$ represents a straight or branched $C_1$-$C_4$ alkyl group or a phenyl group
n may assume values from 2 to 4,
as well as the therapeutically acceptable organic or inorganic salts thereof.

2. Compounds of general formula I according to claim 1, characterized by the fact that they are selected from among:

1-prenyl 3-(3-hydroxy propyl) 1,2-dihydro 2-oxo quinoxaline 1-allyl 3-(3-acetoxy butyl) 1,2-dihydro 2-oxo quinoxaline 1-propyl 3-(3-methylcarbamoyloxy propyl) 1,2-dihydro 2-oxo quinoxaline 1-(2-methycarbamoyloxy ethyl) 3-(3-hydroxy butyl) 1,2-dihydro 2-oxo quinoxaline 1-allyl 3-(3-hydroxy propyl) 7-chloro 1,2-dihydro 2-oxo quinoxaline 1-propargyl -3(3-hydroxy propyl) 6,7-dichloro-1,2-dihydro 2-oxo quinoxaline 1-allyl 3-(4-hydroxy butyl) 1,2-dihydro 2-oxo quinoxaline 1-allyl 3-(3-hydroxy propyl) 1,2-dihydro 2-oxo quinoxaline 1-allyl 3-(3-hydroxy butyl) 1,2-dihydro 2-oxo quinoxaline 1-(methylcrotonyl) 3-(3-hydroxy propyl) 6,7-dichloro-1,2-dihydro 2-oxo quinoxaline 1-propyl 3-(3-hydroxy propyl) 1,2-dihydro 2-oxo quinoxaline 1-crotyl 3-(3-hydroxy propyl) 1,2-dihydro 2-oxo quinoxaline 1-propargyl 3-(3-hydroxy propyl) 1,2-dihydro 2-oxo quinoxaline 1-cinnamyl 3-(3-hydroxy propyl) 1,2-dihydro 2-oxo quinoxaline 1-cyclopropylmethyl 3-(3-hydroxy propyl) 1,2-dihydro 2-oxo quinoxaline 1-cyanomethyl 3-(3-hydroxy propyl) 1,2-dihydro 2-oxo quinoxaline 1-benzyl 3-(3-hydroxy propyl) 1,2-dihydro 2-oxo quinoxaline 1-acetamido 3-(3-hydroxy propyl) 1,2-dihydro 2-oxo quinoxaline 1-crotyl 3-(3-hydroxy butyl) 1,2-dihydro 2-oxo quinoxaline 1-prenyl 3-(3-hydroxy butyl) 1,2-dihydro 2-oxo quinoxaline 1-cyclopropylmethyl 3-(3-hydroxy butyl) 1,2-dihydro 2-oxo quinoxaline 1-(p.nitrobenzyl) 3-(3-hydroxy propyl) 1,2-dihydro 2-oxo quinoxaline 1-propyl 3-(3-hydroxy butyl) 1,2-dihydro 2-oxo quinoxaline 1-(p.methoxybenzyl) 3-(3-hydroxy butyl) 1,2-dihydro 2-oxo quinoxaline 1-methyl 3-(3-hydroxy butyl) 1,2-dihydro 2-oxo quinoxaline 1-butyl 3-(3-hydroxy butyl) 1,2-dihydro 2-oxo quinoxaline 1-(2-pyridyl methyl) 3-(3-hydroxy butyl) 1,2-dihydro 2-oxo quinoxaline 1-pentyl 3-(3-hydroxy butyl) 1,2-dihydro 2-oxo quinoxaline 1-hexyl 3-(3-hydroxy butyl) 1,2-dihydro 2-oxo quinoxaline 1-(3-pyridyl methyl) 3-(3-hydroxy butyl) 1,2-dihydro 2-oxo quinoxaline 1-(4-pyridyl methyl) 3-(3-hydroxy butyl) 1,2-dihydro 2-oxo quinoxaline 1-crotyl 3-(3-methylcarbamoyloxy propyl) 1,2-dihydro 2-oxo quinoxaline 1-propyl 3-(3-isopropylcarbamoyloxy) 1,2-dihydro 2-oxo quinoxaline 1-propyl 3-(3-phenylcarbamoyloxy propyl) 1,2-dihydro 2-oxo quinoxaline 1-(2-acetoxy ethyl) 3-(3-hydroxy propyl) 1,2-dihydro 2-oxo quinoxaline 1-(2-acetoxy ethyl) 3-(3-hydroxy butyl) 1,2-dihydro 2-oxo quinoxaline 1-(2-hydroxy ethyl) 3-(3-hydroxy butyl) 1,2-dihydro 2-oxo quinoxaline 1-(2-hydroxy ethyl) 3-(3-hydroxy propyl) 1,2-dihydro 2-oxo quinoxaline 1-prenyl 3-(5-hydroxy pentyl) 1,2-dihydro 2-oxo quinoxaline.

3. A pharmaceutical composition characterized by the fact that it contains a compound of claim 1 and a pharmaceutically-acceptable carrier.

4. A pharmaceutical composition characterized by the fact that it contains a compound of one of claims 1 or 2 in association with a pharmaceutically acceptable excipient.

5. Method for treatment of respiratory insufficiency comprising the step of administering an effective amount of a compound as defined in claim 1 or 2.

* * * * *